United States Patent
Collins et al.

(10) Patent No.: US 8,960,901 B2
(45) Date of Patent: Feb. 24, 2015

(54) MYOPIA CONTROL OPHTHALMIC LENSES

(75) Inventors: Michael J. Collins, Jollys Lookout (AU); Brett A. Davis, Holland Park (AU); Khaled A. Chehab, Jacksonville, FL (US); Xu Cheng, St. Johns, FL (US); D. Robert Iskander, Bellbowrie (AU)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1377 days.

(21) Appl. No.: 12/697,931

(22) Filed: Feb. 1, 2010

(65) Prior Publication Data
US 2010/0195044 A1 Aug. 5, 2010

Related U.S. Application Data

(60) Provisional application No. 61/149,193, filed on Feb. 2, 2009.

(51) Int. Cl.
G02C 7/04 (2006.01)
G02C 7/02 (2006.01)
A61F 2/16 (2006.01)

(52) U.S. Cl.
CPC .............. *G02C 7/04* (2013.01); *G02C 2202/22* (2013.01); *G02C 7/044* (2013.01); *G02C 2202/24* (2013.01); *G02C 7/027* (2013.01); *A61F 2/1613* (2013.01)
USPC .................................................... 351/159.74

(58) Field of Classification Search
USPC .................. 351/159.73–159.74, 159.77
See application file for complete search history.

(56) References Cited

U.S. PATENT DOCUMENTS

| | | | |
|---|---|---|---|
| 4,495,313 A | 1/1985 | Larsen |
| 4,680,336 A | 7/1987 | Larsen |
| 4,889,664 A | 12/1989 | Kindt-Larsen |
| 5,039,459 A | 8/1991 | Kindt-Larsen |
| 5,057,578 A | 10/1991 | Spinelli |
| 5,314,960 A | 5/1994 | Spinelli |
| 5,371,147 A | 12/1994 | Spinelli |
| 5,540,410 A | 7/1996 | Lust |
| 5,929,969 A | 7/1999 | Roffman |
| 6,045,578 A | 4/2000 | Collins et al. |
| 6,260,966 B1 | 7/2001 | Sawano et al. |
| 6,554,425 B1 | 4/2003 | Roffman et al. |
| 7,025,460 B2 | 4/2006 | Smitth et al. |
| 7,036,931 B2 | 5/2006 | Lindacher et al. |
| 7,178,918 B2 | 2/2007 | Griffin |
| 7,300,152 B2 | 11/2007 | Jones et al. |
| 7,341,345 B2 | 3/2008 | Azar et al. |

(Continued)

FOREIGN PATENT DOCUMENTS

| EP | 1853961 A1 | 11/2007 |
|---|---|---|
| EP | 1853961 A4 | 4/2009 |

(Continued)

OTHER PUBLICATIONS

International Search Report PCT/US2010/022815 Date of Mailing Apr. 23 2010.

(Continued)

*Primary Examiner* — Ricky Mack
*Assistant Examiner* — Robert E Tallman

(57) ABSTRACT

Lenses are designed using wavefront measurements amenable to correction factors for near and far vision as well as pupil size to slow or stop myopia progression.

5 Claims, 20 Drawing Sheets

(56) References Cited

U.S. PATENT DOCUMENTS

| | | | |
|---|---|---|---|
| 7,370,962 B2 | 5/2008 | Roffman et al. | |
| 7,374,286 B2 | 5/2008 | Fujieda et al. | |
| 7,377,641 B2 * | 5/2008 | Piers et al. | 351/159.05 |
| 7,766,482 B2 | 8/2010 | Smith et al. | |
| 7,832,859 B2 | 11/2010 | Phillips | |
| 8,079,704 B2 | 12/2011 | Sanger | |
| 8,485,662 B2 | 7/2013 | Collins et al. | |
| 2003/0058404 A1 | 3/2003 | Thorn et al. | |
| 2008/0309882 A1 | 12/2008 | Thorn et al. | |
| 2009/0210054 A1 * | 8/2009 | Weeber et al. | 623/6.11 |

FOREIGN PATENT DOCUMENTS

| | | |
|---|---|---|
| JP | 02/131705 A | 11/1990 |
| JP | 9026559 A | 1/1997 |
| JP | 11258554 A | 9/1999 |
| JP | 04/519707 A | 7/2004 |
| JP | 06/026242 A | 2/2006 |
| JP | 06/505008 A | 2/2006 |
| JP | 06/515938 A | 6/2006 |
| JP | 07/511803 A | 5/2007 |
| JP | 08/502942 A | 1/2008 |
| JP | 08/506505 A | 3/2008 |
| JP | 08/530598 A | 8/2008 |
| JP | 08/250316 A | 10/2008 |
| JP | 05039059 B2 | 10/2012 |
| WO | WO 0232297 | 4/2002 |
| WO | WO 2005/124433 A2 | 12/2005 |
| WO | WO 2006014624 A2 | 2/2006 |

OTHER PUBLICATIONS

Notification of Reasons for Rejection from the Japanese Patent Office for Application No. 2011-548387 dated Jan. 7, 2014.

* cited by examiner

US 8,960,901 B2

MYOPIA CONTROL OPHTHALMIC LENSES

CROSS-REFERENCES TO RELATED APPLICATIONS

This application claims the benefit of U.S. Provisional Application No. 61/149,193, filed Feb. 2, 2009, which is hereby incorporated by reference in its entirety.

BACKGROUND OF THE INVENTION

This invention relates to designs and methods for preventing, stopping or slowing myopia progression.

Myopia, also known as short-sightedness, is a refractive condition wherein the overall power of the eye is too high, or too strong, causing light from distant objects to focus in front of the retina. This is perceived by the viewer as blurring of distant objects, with the amount of blurring being related to the severity of the myopia. This condition is often first seen in childhood, and usually noticed at school age. A progression, or increase, in the severity of myopia, is usually seen in myopic cases until young adulthood.

U.S. Pat. No. 6,045,578 proposes methods of using on-axis longitudinal spherical aberration (LSA) in contact lens designs to attempt to halt myopia progression. The design approach suggested does not appear to address specific wavefront/refractive power characteristics of the individual eye/or group average data or changes in pupil size associated with close work.

U.S. Pat. No. 7,025,460 proposes methods of altering field curvature (off-axis focal point variation) to try to halt myopia progression. The mathematics behind this approach uses "extended conics" where the simple conic equations have even ordered polynomial terms added to them. These conic and polynomial terms are processed so that the contact lens surface shape of the proposed design produces the required amount of field curvature. This approach addresses off-axis design. On-axis optical design of the lens does not appear to have been addressed. Pupil size and wavefront changes associated with near tasks were not addressed.

US 2003/0058404 and US 2008/0309882 proposes a method of measuring the wavefront of the eye and correcting the wavefront of the eye with a customized correction to slow myopia progression. This did not include measuring the wavefront for a near stimulus distance and does not appear to suggest considering the difference between the wavefront measured for a far stimulus and a near stimulus. Pupil size changes associated with near tasks were also not an aspect of the design process.

EP 1853961 proposes the measurement of the wavefront before and after near work. The changes in wavefront aberrations are then corrected with a custom contact lens. This does not include the difference in wavefront measured for a far and near stimulus as only the wavefront before and after near work are addressed. It does not consider the pupil size changes associated with near tasks in the design process. Group or population data to create a design to control eye growth are not included.

A more complete approach to slowing or stopping myopia progression is still desired. This is addressed in this specification.

SUMMARY OF THE INVENTION

In one aspect of the invention a method and resulting design to be used in the fabrication of ophthalmic lenses useful in controlling and slowing the progression of myopia incorporates the use of wavefront data from the eye. Ophthalmic lenses include, for example, contact lenses, intraocular lenses, corneal inlays, and corneal onlays. Further, they can include patterns for corneal refractive surgery such as LASIK surgery.

In another aspect of the invention, the method and designs used to make lenses for slowing myopia are used in patients with active levels of accommodation.

In yet another aspect of the invention, a design for an ophthalmic lens produced according to the methods of the invention includes a convex surface with a central optic zone surrounded by a peripheral zone which is further surrounded by an edge zone, and a concave surface which rests on the wearer's eye; and a lens power at any location in the optical zone is described by the sum of the apical on axis distance averaged wavefront derived power plus a correction which is derived from a single, partial multiple or multiple of the difference between the distance and near average wavefront derived power at each location (x) and the difference between the apical near and distance wavefront derived powers; the lenses made using these designs are useful in controlling or slowing the progression of myopia.

In another aspect of the invention, a method to generate an ophthalmic lens design includes the steps of acquiring wavefront data, converting the wavefront data to a radial power map, and generating a lens power profile.

In yet another aspect of the invention, total population wavefront data is considered.

In yet another aspect of the invention, data for a sub-population wavefront data is considered.

In yet another aspect of the invention, data for an individual subject is considered.

In yet another aspect of the invention, the wavefront data is an average of multiple wavefront files.

In yet another aspect of the invention, the lens design power profile is calculated by averaging all meridians to a rotationally symmetric form.

In yet another aspect of the invention, the lens design power profile is calculated by the inverse of the near power profile.

In yet another aspect of the invention, the lens design power profile is calculated by neutralizing the negative aberration of the near power profile.

In yet another aspect of the invention, the lens design power profile is calculated by adding the distance to the near wavefront power profiles.

In yet another aspect of the invention, the lens design power profile is calculated by adding a multiple of the distance to the near wavefront power profiles.

In yet another aspect of the invention, the lens design power profile is calculated by adding a portion of the distance to the near wavefront power profiles.

In yet another aspect of the invention, methods of designing lenses for slowing myopia progression are encoded into instructions such as machine instructions and are programmed into a computer.

In yet another aspect of the invention, articles include executable instructions for designing lenses for slowing myopia progression; the method includes converting wavefront data characterizing an eye to a radial power map, generating a lens power profile and using the power profile to produce a lens design for a lens with a convex surface with a central optic zone surrounded by a peripheral zone which is further surrounded by an edge zone, and a concave surface which rests on the wearer's eye; the lens power at any location in the optical zone is described by the sum of the apical distance averaged wavefront derived power plus a correction which is derived from a single, partial multiple or multiple of the difference between the distance and near average wavefront derived power at each location and the difference between the apical near and distance wavefront derived powers.

DETAILED DESCRIPTION

The methods of the invention involve using wavefront data to design and produce contact lenses useful for treating, slowing, and sometimes stopping the progression of myopia. Ocular wavefront data, for both distance and near stimulus levels is collected from a patient using a wavefront sensor such as a COAS (Wavefront Sciences Inc, Albuquerque N.M.). This wavefront data is generally in the form of Zernike polynomial coefficients but can also be a set of wavefront heights at specified Cartesian or polar coordinates. A preferred system to designate the Zernike coefficients has been described as the OSA method, in ANSI Z80.28.

The method to design lenses for individuals on a custom lens basis or averaged for populations, or sub-populations. This method can be used to produce a rotationally symmetric design where all optic zone meridians are the same, or a non-rotationally symmetric design where each meridian is unique and the result of wavefront analysis. In some embodiments, known changes in size of the pupil due to accommodation or luminance are taken into account.

A preferred method for generating ophthalmic lens designs is based in part upon ocular wavefront data and includes the following steps.

Figure 1:
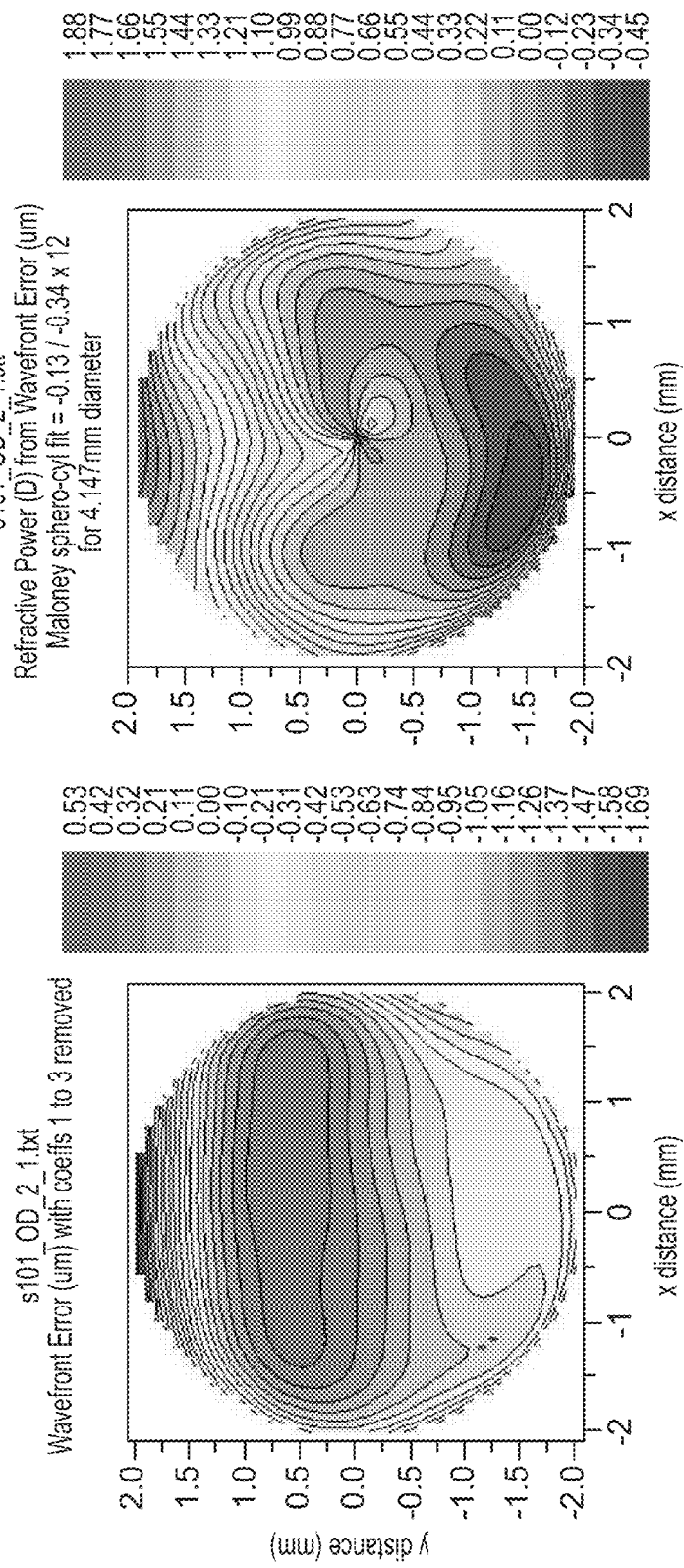
FIG. 1 shows the wavefront error on the left panel and calculated refractive power on the right panel, both for the same eye.

1. Ocular wavefront data, for distance and near stimulus levels, is collected from patients using a wavefront sensor.
2. Each wavefront is converted to a refractive power map by estimating the radial slopes in the direction of the z axis, defined as the front to back axis, e.g. along the visual axis through the pupil center.
3. Calculating the axial focal lengths (i.e. the intersection of the radial 'normal' with the z axis) and converting the focal lengths to optical power values (FIG. 1).

In another embodiment of the method, a refractive power map is calculated from the set of estimated wavefront Zernike coefficients using the refractive Zernike power polynomials, $\Psi_j(\rho,\theta)$, as follows (see Iskander et al 2007, attached)

$$\hat{F}(r, \theta) = \frac{10^3}{r_{max}} \sum_{j=3}^{P-1} c_j \Psi_j(r/r_{max}, \theta) \quad (1)$$

where $c_j$ are the wavefront Zernike polynomial coefficients, $r_{max}$ corresponds to the pupil radius, $$\Psi_j(\rho, \theta) = \begin{cases} \sqrt{2(n+1)}\, Q_n^m(\rho)\cos(m\theta), & m > 0 \\ \sqrt{2(n+1)}\, Q_n^m(\rho)\sin(m\theta), & m < 0 \\ \sqrt{n+1}\, Q_n^m(\rho) & m = 0 \end{cases} \quad (2)$$

with $$Q_n^m = \sum_{s=0}^{(n-|m|)/2-q} \frac{(-1)^s(n-s)!(n-2s)}{s!((n+|m|)/2-s)!((n-|m|)/2-s)!} \rho^{n-2s-2} \quad (3)$$

and $$q = \begin{cases} 1, & |m| \leq 1 \\ 0, & \text{otherwise} \end{cases}$$

Ocular pupil sizes are also estimated either directly from the wavefront measurement or by an independent pupil measurement (e.g. using a pupillometer). If the pupil is measured independently of the wavefront, it should be measured under similar lighting conditions and with the patient focused on a far target and a near target that produces the same accommodation stimulus levels as those used when the wavefronts were measured (for example 0 D and 3 D accommodation stimulus levels). To get wavefront maps of sufficient diameter, measuring the wavefront in moderate to low luminance conditions is preferred. The far and near wavefronts should be measured in the same luminance conditions, less than or equal to 50 candela per meter squared, for example The ophthalmic lens made according to the invention have the following parts and characteristics:
a) a convex surface with a central optic zone surrounded by a peripheral zone which is further surrounded by an edge zone, and a concave surface which rests on the patient's eye;
b) the lens power at any location in the optical zone is described by the sum of the apical distance averaged wavefront derived power plus a correction which is derived from a single, partial multiple or multiple of the difference between the distance and near average wavefront derived power at each location (x) and the difference between the apical near and distance wavefront derived powers, the optical lens power is useful in controlling or slowing the progression of myopia.

The data files are put through a screening process where the wavefront Zernike coefficients, pupil sizes and refractive power maps are analysed to identify trends in the wavefront dynamics and remove outliers or invalid data (eg. using the Wavefront File Management software).

If multiple wavefront data sets have been collected (as is preferred), the refractive power maps can be averaged to reduce random errors and variability associated with factors such as microfluctuations of accommodation.

Figure 2:
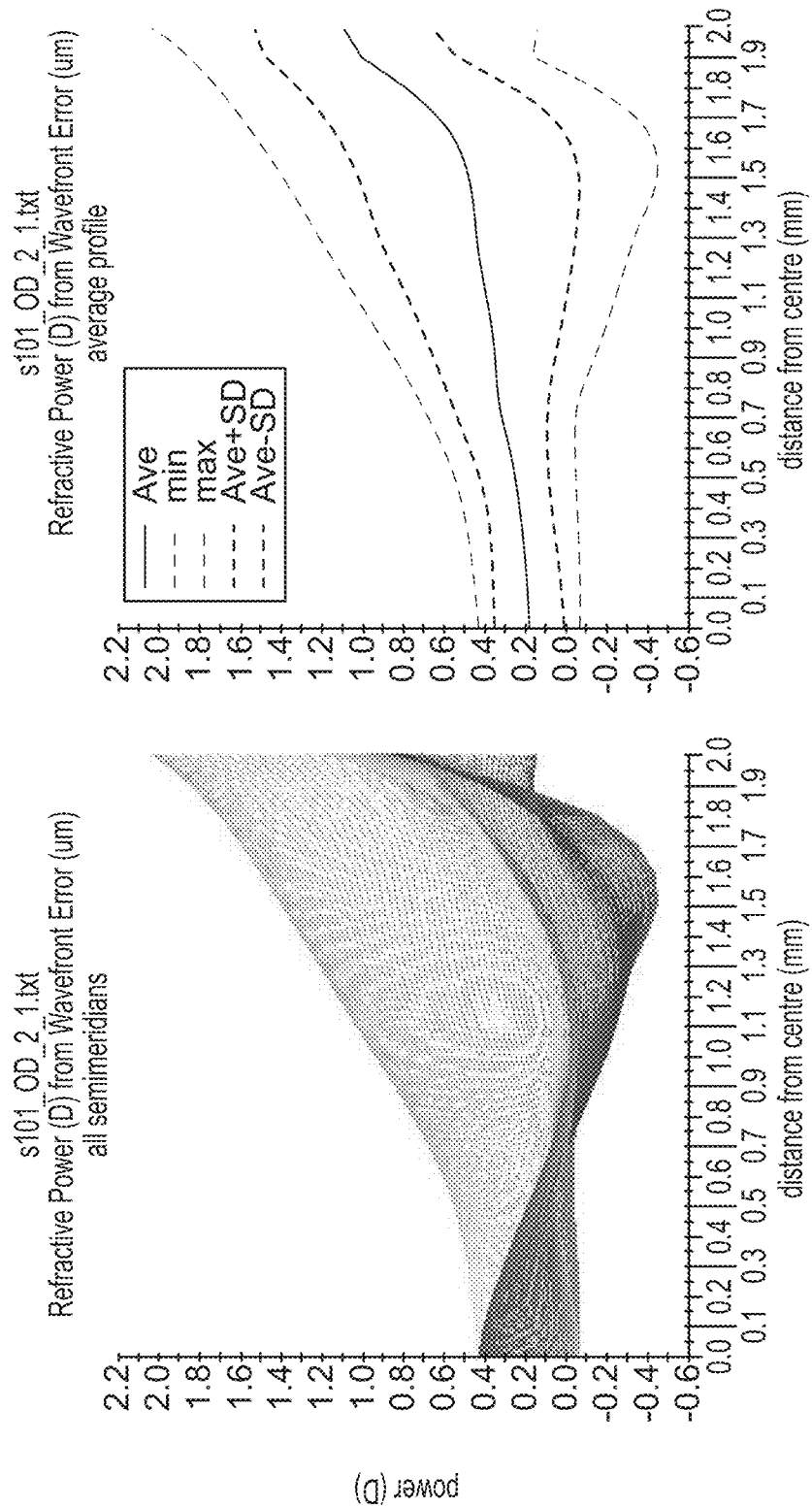
FIG. 2 shows profile plots of refractive power data in terms of distance from center. The left panel shows all available meridians, the right panel shows the average, maximum and minimum profiles.

The next step in the process is to generate an average refractive power profile. This is calculated by averaging all considered semi-meridians of the refractive power data (i.e. calculate the average in terms of radial polar coordinate, disregarding the azimuthal/meridional angular coordinate). This profile can be generated for individual or group mean data. If it is assumed, as is preferred, that the azimuthal frequency is not likely to be of significant interest above $4^{th}$ order, then there should be a minimum of 8 meridians. Preferably there should be at least 32 meridians. Shown in FIG. 2 are profile plots of refractive power data in terms of radial coordinate (distance from centre). Data from all of the measured semi-meridians is shown on the left. This can be used for non-rotationally symmetrical designs. Average, maximum and minimum refractive power profiles are shown on the right. This average can be calculated in the manner of any conventional arithmetic averaging, including but not limited to arithmetic mean, median or geometric mean. This can be used for individual customized or population based rotationally symmetric designs.

Figure 3:
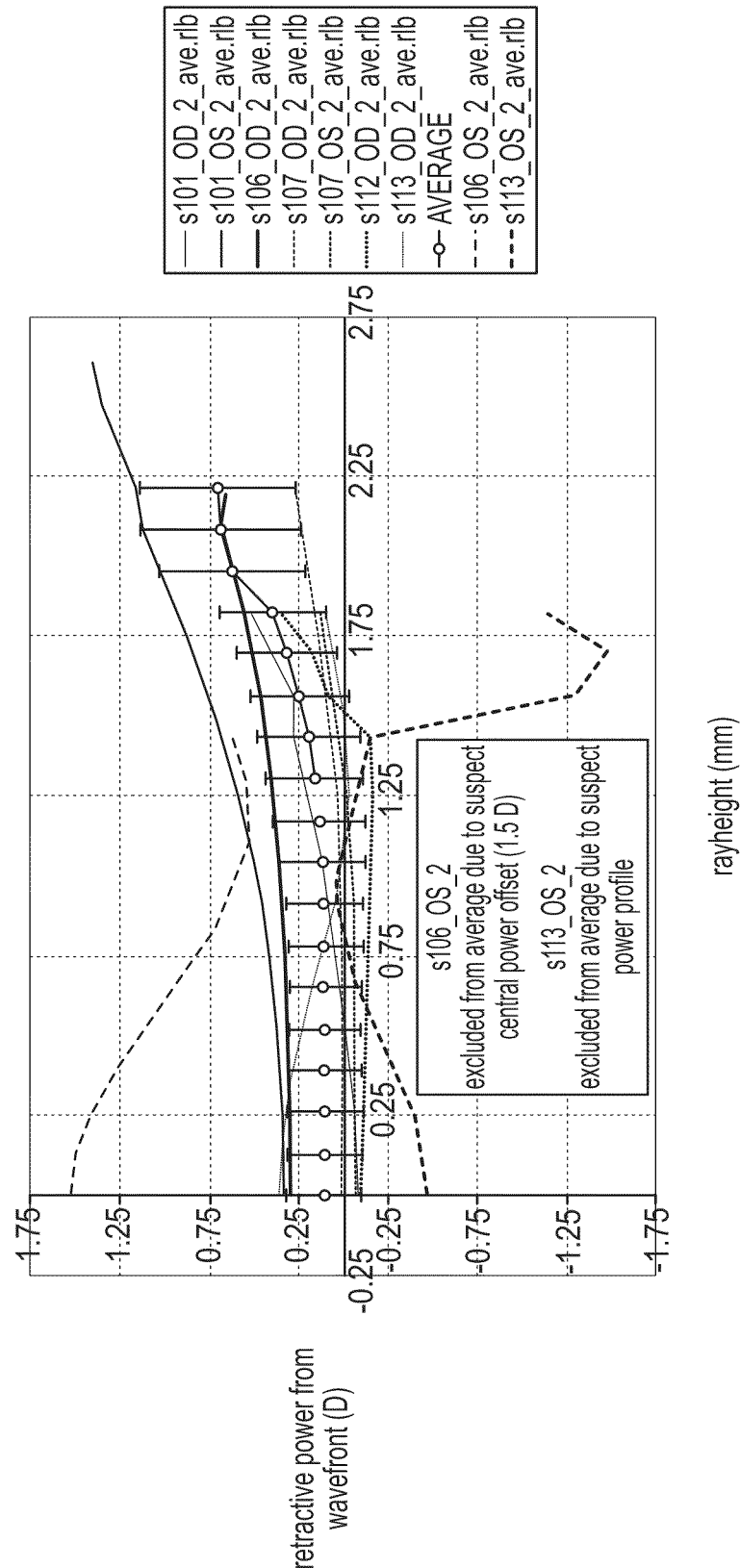
FIG. 3. is a graph of the average refractive power profiles for individuals and the group average for an accommodation stimulus at 3 m distance.

In FIG. 3 are the average right eye refractive power profiles for individuals and the group average for an accommodation stimulus at 6 m distance (i.e. accommodation stimulus is 0.17 D). This is approximately distance (far) vision.

Figure 4:
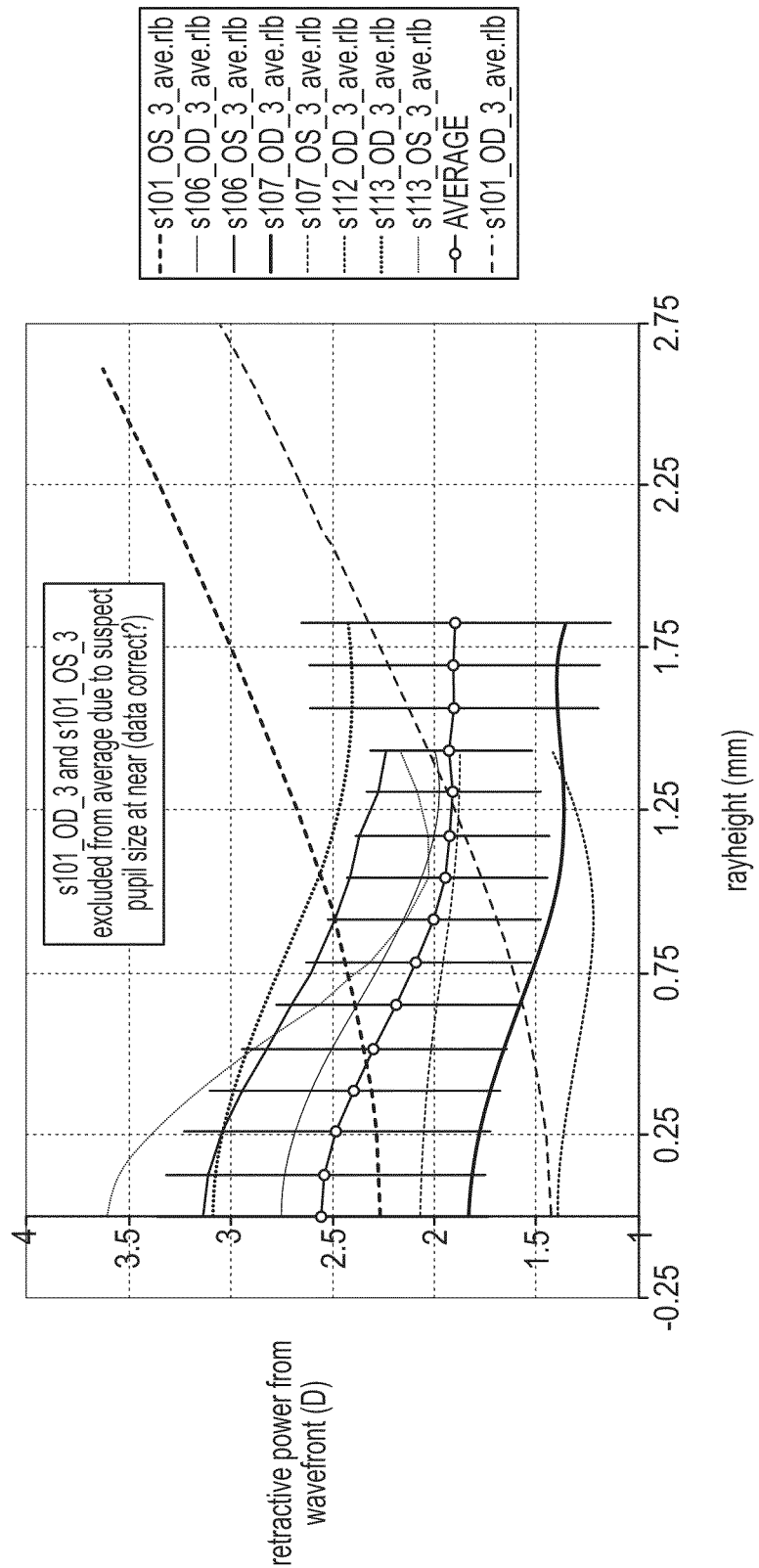
FIG. 4. is a graph of the average refractive power profiles for individuals and the group average for an accommodation stimulus at 0.33 m distance.

In FIG. 4 are the average left eye refractive power profiles for individuals and the group average for an accommodation stimulus at 0.33 m distance (i.e. accommodation stimulus is 3.00 D). This represents near vision.

Figure 5:
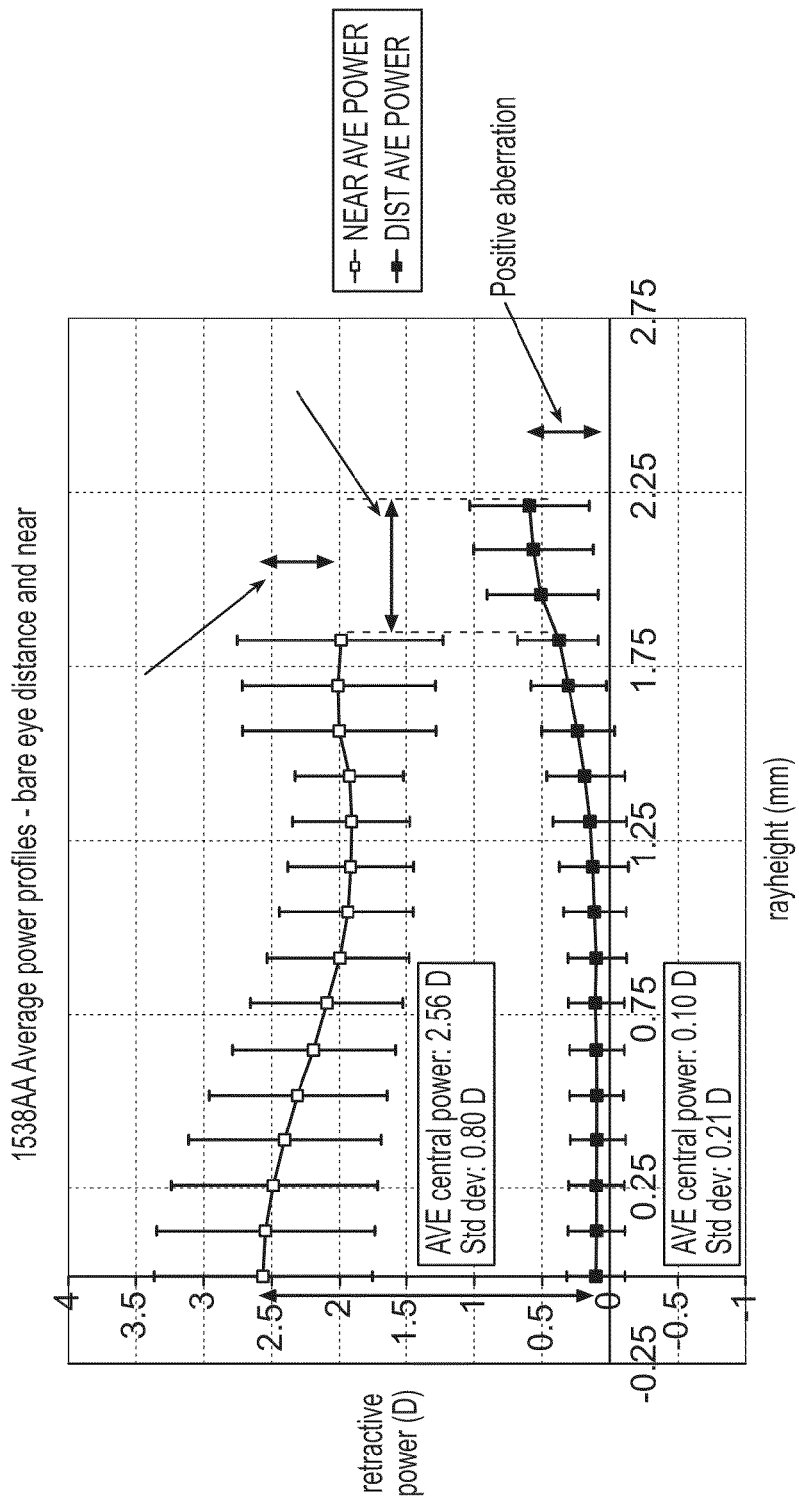
FIG. 5. shows the group average refractive power profiles for both the distance and near stimulus levels.

The group average refractive power profiles for both the distance and near stimulus levels are shown together in FIG. 5. These data are then used to determine the required refractive power profile of the lens for myopia control.

Power Profile Driven Ophthalmic Lens Design Methods:

Different data sources can be used to derive a contact lens design for myopia control. Examples include:
A customized design based on the individual subjects data, or
A group design based on a particular sub-population of data (e.g. young Asian children aged 10-16 years of age), or
A general population design based on all available data (e.g. all myopes).

Additionally, both rotationally symmetric designs or non-rotationally symmetric designs are obtainable using the method of the invention. When data is averaged across all considered semi-meridians (see FIG. 5) it can be used to create rotationally symmetrical designs, or
If the data is retained in its semi-meridional form (left panel of FIG. 2), it can be used to create non-rotationally symmetric designs. Non-rotationally symmetric correction forms include, but are not limited to toric, sphero-cylindrical, sphero-cylindrical with higher order aberration correction. Toric includes the correction of both regular and irregular astigmatism.

Further refinement of the design produced according to the invention can be based on the pupil size of the subject (or population of subjects). The natural pupil size for near accommodation levels is typically smaller than that for distance/far accommodation levels. Therefore for an optical design based on foveal vision (on-axis), the change in optical power required to control eye growth based on the near wavefront can be confined to an optical zone diameter corresponding to the smaller pupil present when the near wavefront is measured. Outside of this inner central region, the optical design can revert to one that is relevant for distance vision.

The following are exemplary design methods obtained using averaged data from all of the considered semi-meridians. These approaches will result in rotationally symmetrical designs (no requirement for them to be stabilized to minimize lens rotation).

Figure 6:
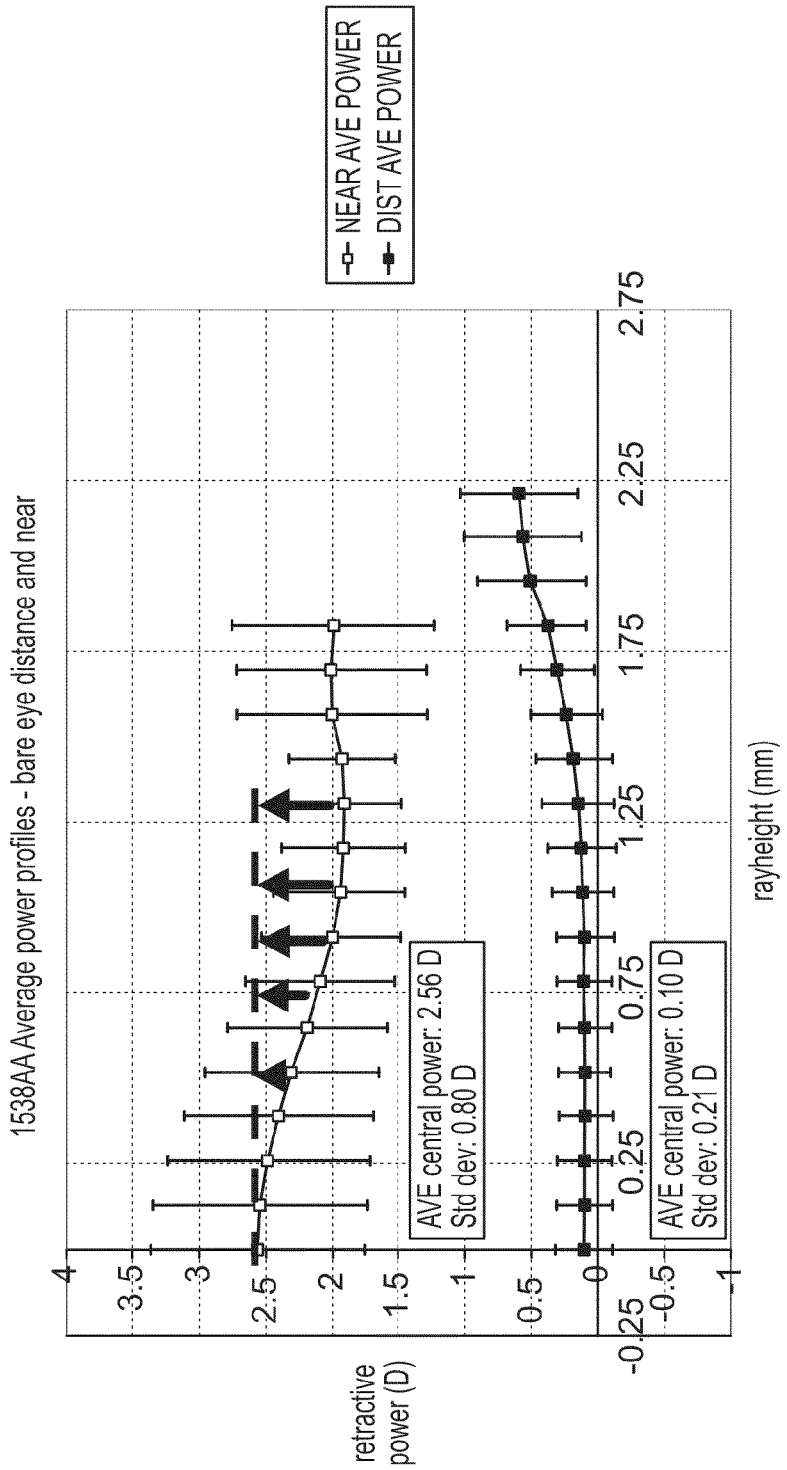
FIG. 6 shows the amount of increase in power is designed to neutralize the natural negative power shift in the group average data for the near wavefront power.

Method 1:

In the first method, the meridian averaged, near wavefront refractive power is used as the starting point for the design. The design requires an increase in refractive power of the lens (more positive power) with increasing chord diameter from the centre of the lens. The amount of increase in power is designed to neutralize the natural negative power shift that is evident in the group average data for the near wavefront power (FIG. 6). The black arrows indicate the positive power change required. Thus the near wavefront is corrected to a zero power change.

Figure 7:
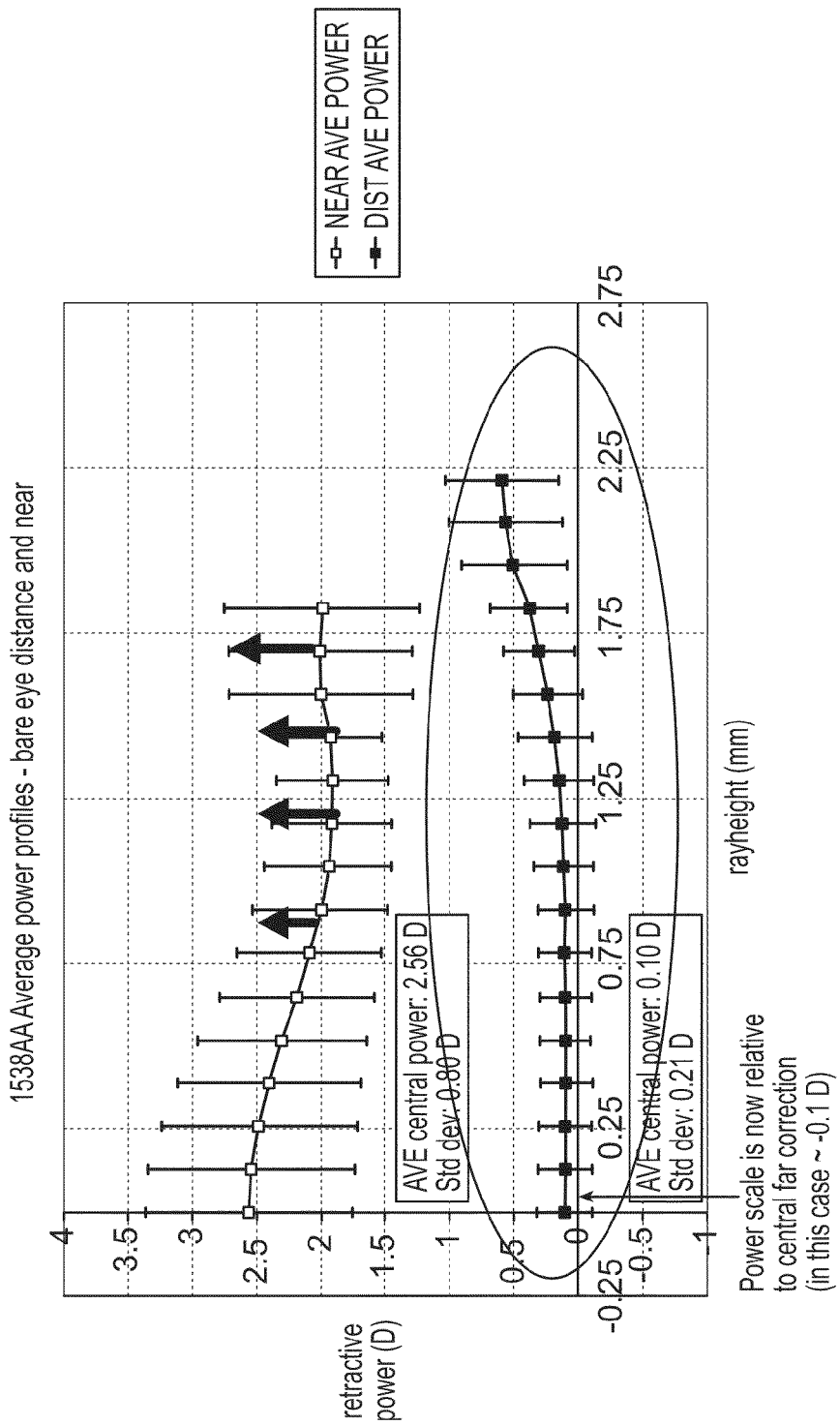
FIG. 7 shows the amount of increase in power is designed to shift the natural negative power shift which is evident in the group average data for the near wavefront power back to the distance wavefront power profile.
Figure 8:
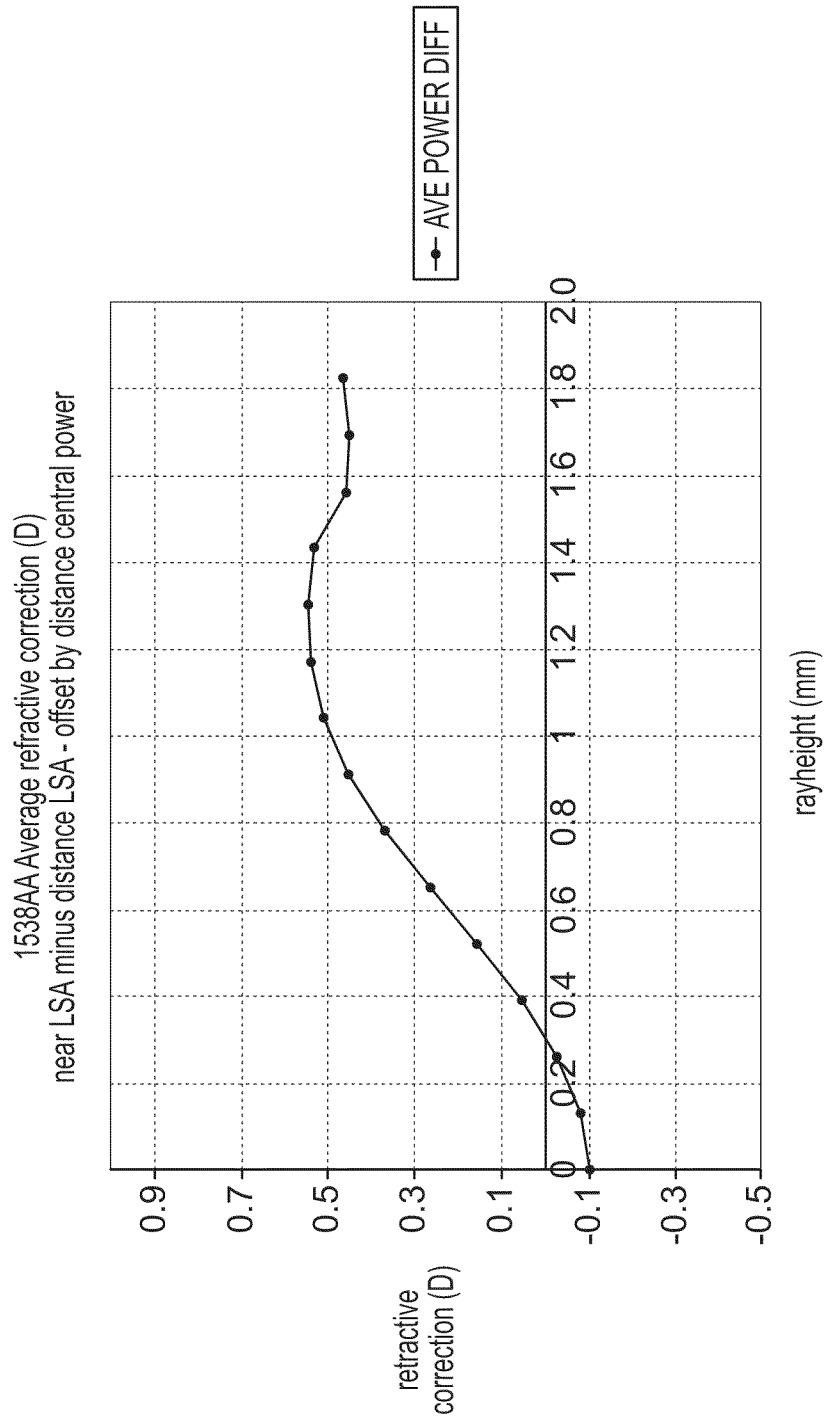
FIG. 8 shows a final lens power profile based upon the method described herein.

Method 2:

In the second method, the meridian averaged, near wavefront refractive power is again used as the starting point for the design. However the target power change in this case is the meridian averaged, distance wavefront refractive power. The design requires an increase in refractive power of the lens (more positive power) with increasing chord diameter from the centre of the lens. The amount of increase in power is designed to shift the natural negative power shift which is evident in the group average data for the near wavefront power back to the distance wavefront power profile (FIG. 7). The black arrows indicate the positive power change required. If the patient needed a −3.00 D distance correction, the lens power profile in this case would be −3.00 D centrally, at a ray height of 0.6 mm the required increase in power would be about 0.25 D (net power −2.75), at 1 mm ray height the required increase in power would be about 0.5 D (net power −2.50 D). FIG. 7 represents the wavefront derived power profile and FIG. 8 shows a lens design power profile to correct both the central error and the profile going to the periphery based upon the rationale described above. While this example shows the actual design extending out to a ray height of 1.6 mm (diameter of 3.2 mm) it is appreciated that if the wavefront were measured to a larger diameter, the design would extend out further. It is also appreciated that the design could be extrapolated to as far as 4 mm ray height by suitable mathematical methods.

FIG. 8 shows a final lens power profile based upon the method described herein.

Figure 9:
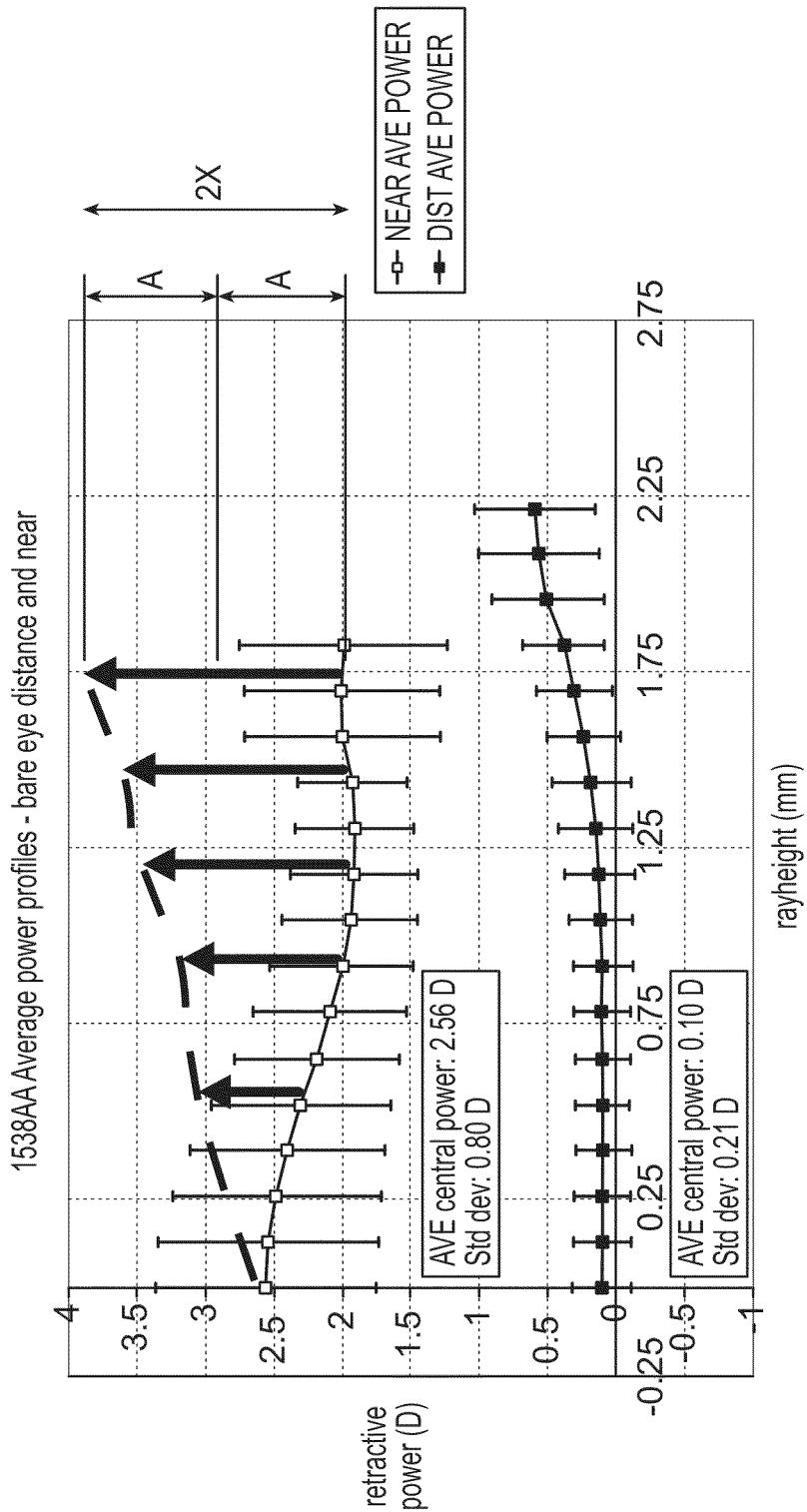
FIG. 9 shows the amount of increase in power is designed to shift the natural negative power shift which is evident in the group average data for the near wavefront power back to greater than the distance wavefront power profile.

Method 3:

In another embodiment of the invention, the meridian averaged, near wavefront's refractive power is again used as the starting point for the design. However the target power change in this case is double the difference to reach the meridian averaged, distance wavefront refractive power. Double the difference is preferred, but the difference can range up to 4 times the distance wavefront refractive power. The design requires an increase in refractive power of the lens (more positive power) with increasing chord diameter from the centre of the lens. The amount of increase in power is designed to shift the natural negative power shift which is evident in the group average data for the near wavefront power back to more than the distance wavefront power profile (FIG. 9). The black arrows indicate the positive power change required. It is also recognized that multipliers of less than unity are useful, for example 0.5 the difference. This may be closer to natural vision for the patient, but still embodies the tenets of this invention.

In methods 1-3, the design power profiles were calculated as follows: The optical power profiles were described mathematically by the equation:

$$\text{PowProf} = RPD_{(0)} + k_{(x)}((RPD_{(x)} + (RPN_{(0)} - RPD_{(0)})) - RPN_{(x)})$$

Where $RPD(x)$ is the average wavefront derived distance refractive power measured at distance at a ray height x, $RPN(x)$ is an average wavefront derived near refractive power measured at near at a ray height x, and $k(x)$ is any suitable mathematical function, for example a constant multiplier, the preferred values for which are between 1 to 2 but the usable range extends from 0.25 to 4, or vary with x as with an inverse Stiles Crawford effect. In selected cases, the function RPD can be replaced with a flat line with a slope of zero. $RPD(0)$ is the average wavefront derived distance apical refractive power, and $RPN(0)$ is the average wavefront derived near apical refractive power measured at near at a ray height x.

In methods 4-6, data from all considered semi-meridians (not averaged across semi-meridians) are used. This approach results in non-rotationally symmetrical designs. These designs must be stabilized to minimize lens rotation.

Method 4

In this embodiment of the invention the semi-meridian near wavefront's refractive power is used as the starting point for the design. The design requires an increase in refractive power of the lens (more positive power) with increasing chord diameter from the centre of the lens. The amount of increase in power is designed to neutralize the natural negative power shift that is evident in the data for the near wavefront power.

For every meridian and chord location where the power is negative, the power will be changed back to zero. This approach is analogous to Method 1, but applied to all locations across all meridians (not just the average meridian data as in Method 1).

Methods 5 and 6:

These methods are also analogous to Methods 2 and 3 (respectively). In Method 5, each location of the power profile that is negative in power for the near wavefront is shifted to match the corresponding point of the distance wavefront. In the vast majority of instances, the distance wavefront will have positive power change at each location, but may in some instances be negative in power change.

In Method 6, each location of the power profile that is negative in power for the near wavefront is shifted by double the power required to match the corresponding point of the distance wavefront. If the distance wavefront power change profile happens to be negative in power at any location, the design approach can be modified to make the default power at this location equal to zero.

Method 7:

The wavefront diameter for a near stimulus, is approximately 3.5 mm (ray height 1.75 mm), while for the distance wavefront it is approximately 4 mm (ray height 2 mm). The power profile within the central 3.5 mm (in this case) can be designed based on Methods 1 to 6 described above. From the edge of 3.5 mm central region to the edge of the optical zone (e.g. 7 mm) the lens power change can be designed to follow the power change derived from the distance wavefront (see black arrows from 1.75 to 2 mm in distance wavefront). If the distance wavefront does not extend to the edge of the 7 mm optic zone, the power progression could be an extrapolation of the distance power profile change or asymptote in power.

This design approach attempts to limit any vision loss associated with the near wavefront correction to control eye growth. It does this by providing correction tailored more towards the distance wavefront for the optical region of the lens (peripheral region of the optic zone) that becomes "active" when the pupil becomes larger when viewing in the distance.

An alternative approach, that does not optimize vision for distance but enhances the eye growth control, is to extrapolate the near wavefront power profile change from the edge of the near wavefront out to the edge of the 7 mm optical zone.

Figure 10:
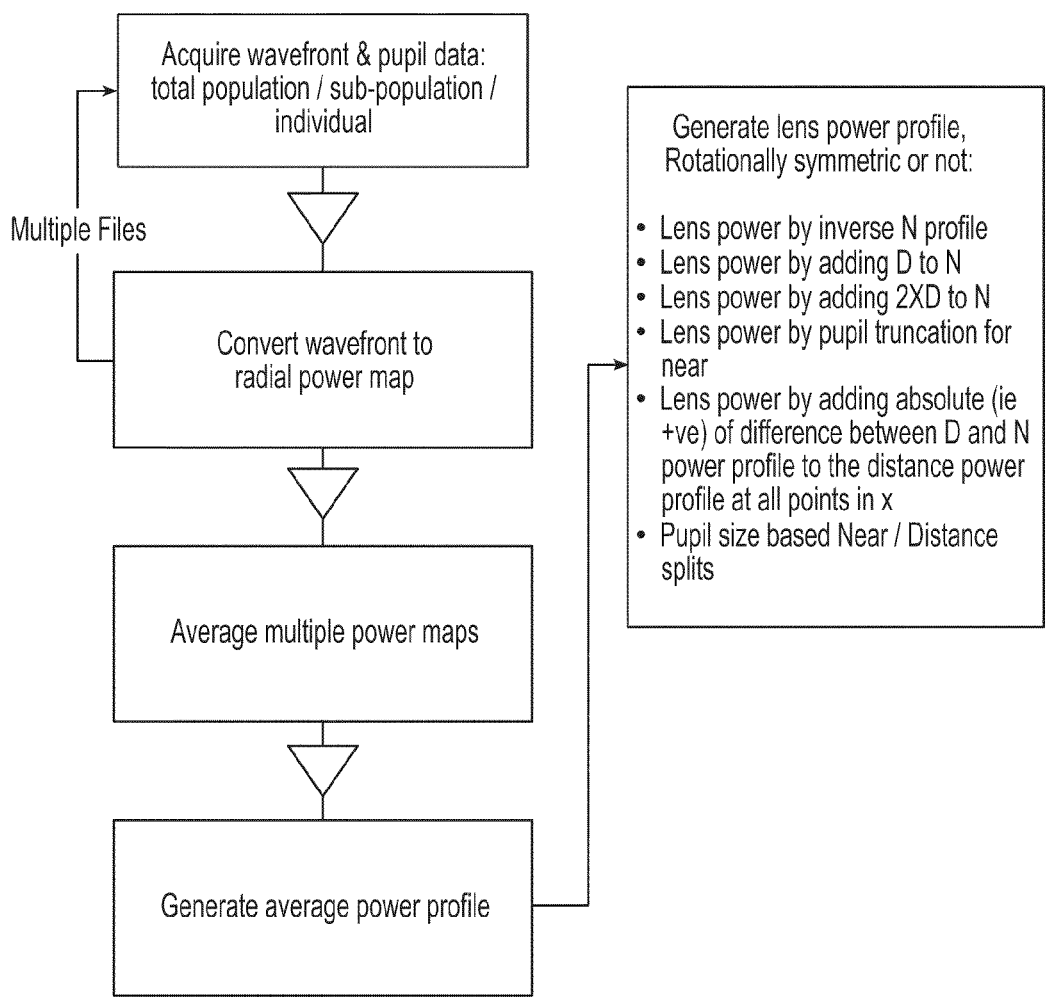
FIG. 10 shows the flow of information in the practice of an aspect of the inventive method.

The flow of information to practice this method is shown in FIG. 10.

Figure 11A:
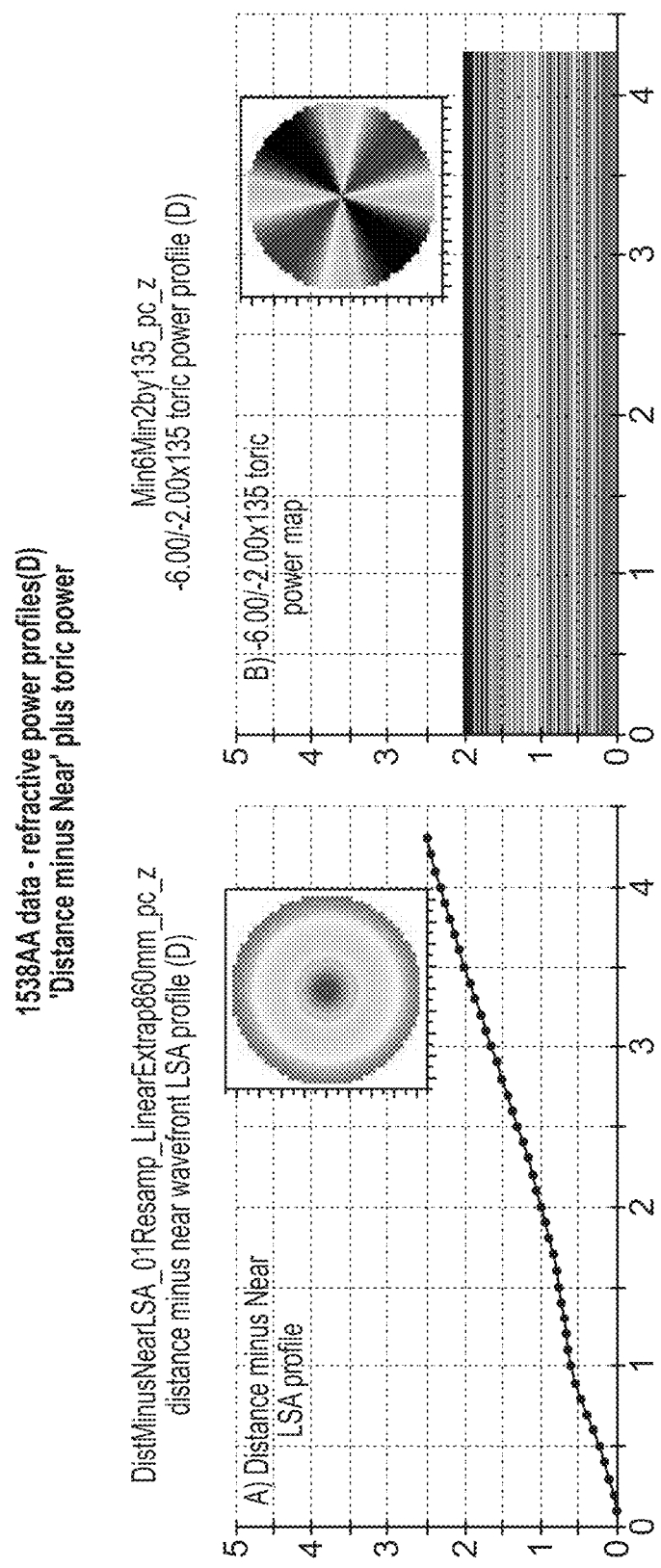
FIGS. 11A-11B show power profiles of lenses designed according to an aspect of the inventive method.
Figure 11B:
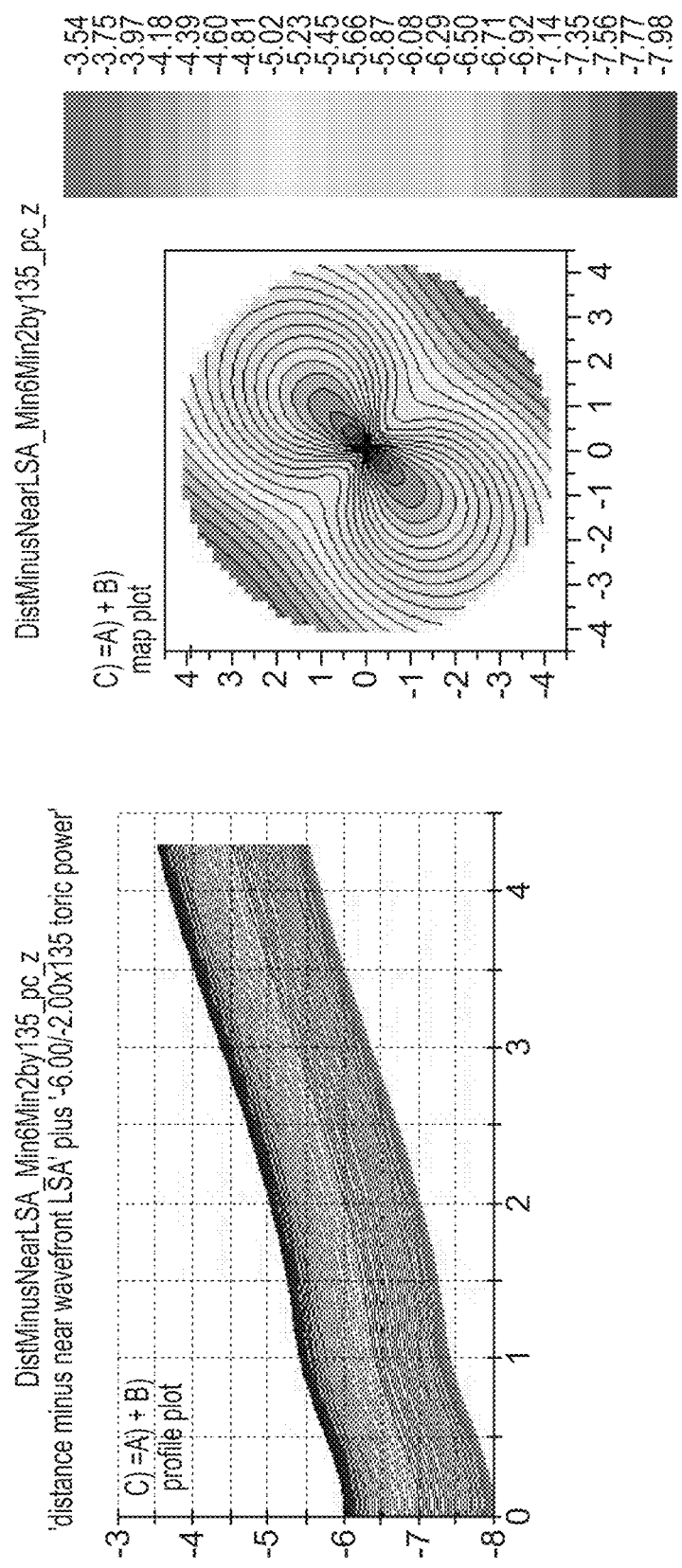

The application of this method to create a specific astigmatic or toric design is shown in FIG. 11. In FIG. 11A, the power profile that was derived by subtracting the distance minus the near wavefront derived averaged power values is shown. In FIG. 11B, the meridians of a conventional toric lens with a power of −6.00DS−2.00 DC×135 is shown.

Figure 12A:
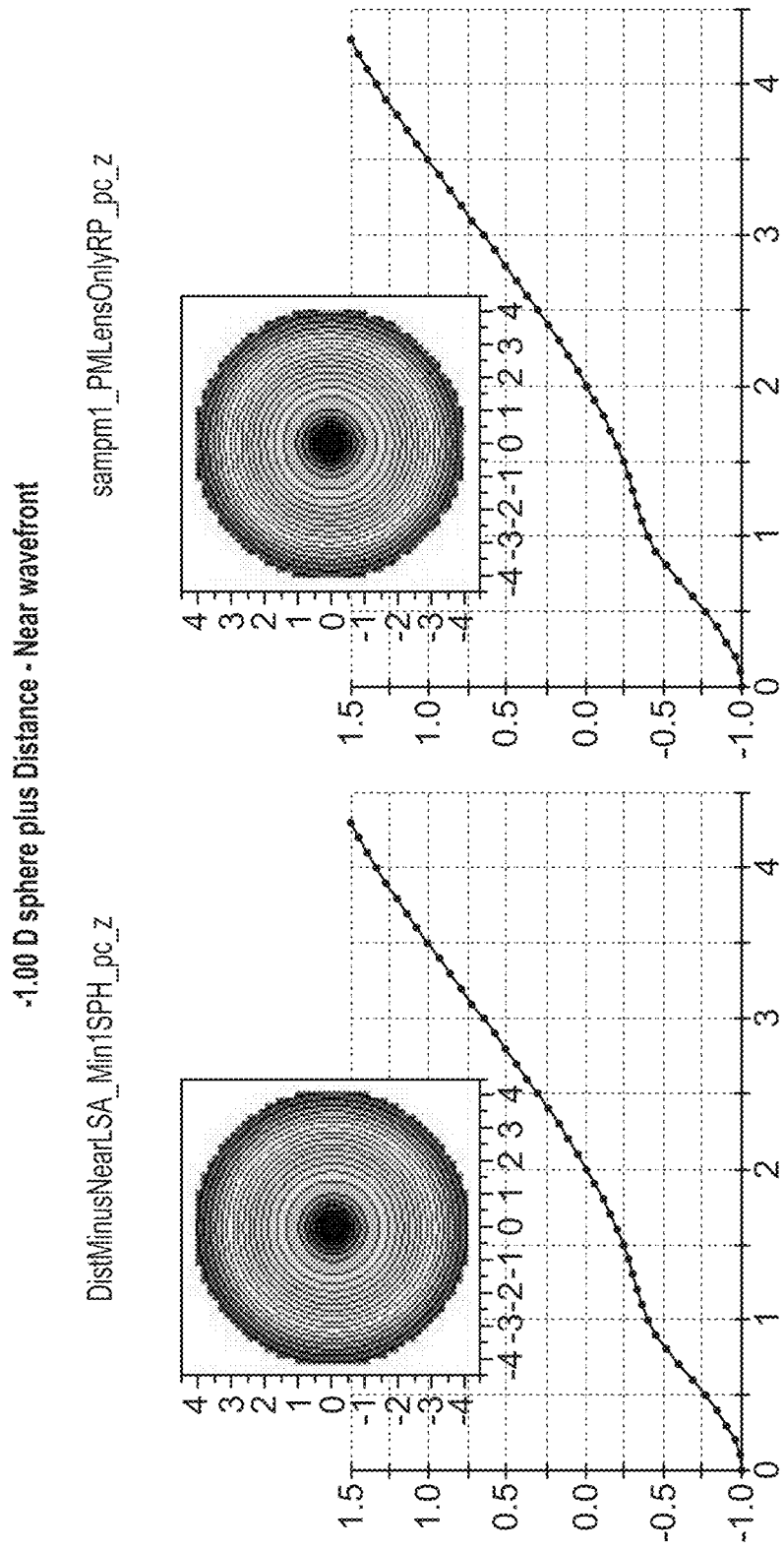
FIGS. 12A-12C show power profiles of lenses designed according to an aspect of the inventive method.
Figure 12B:
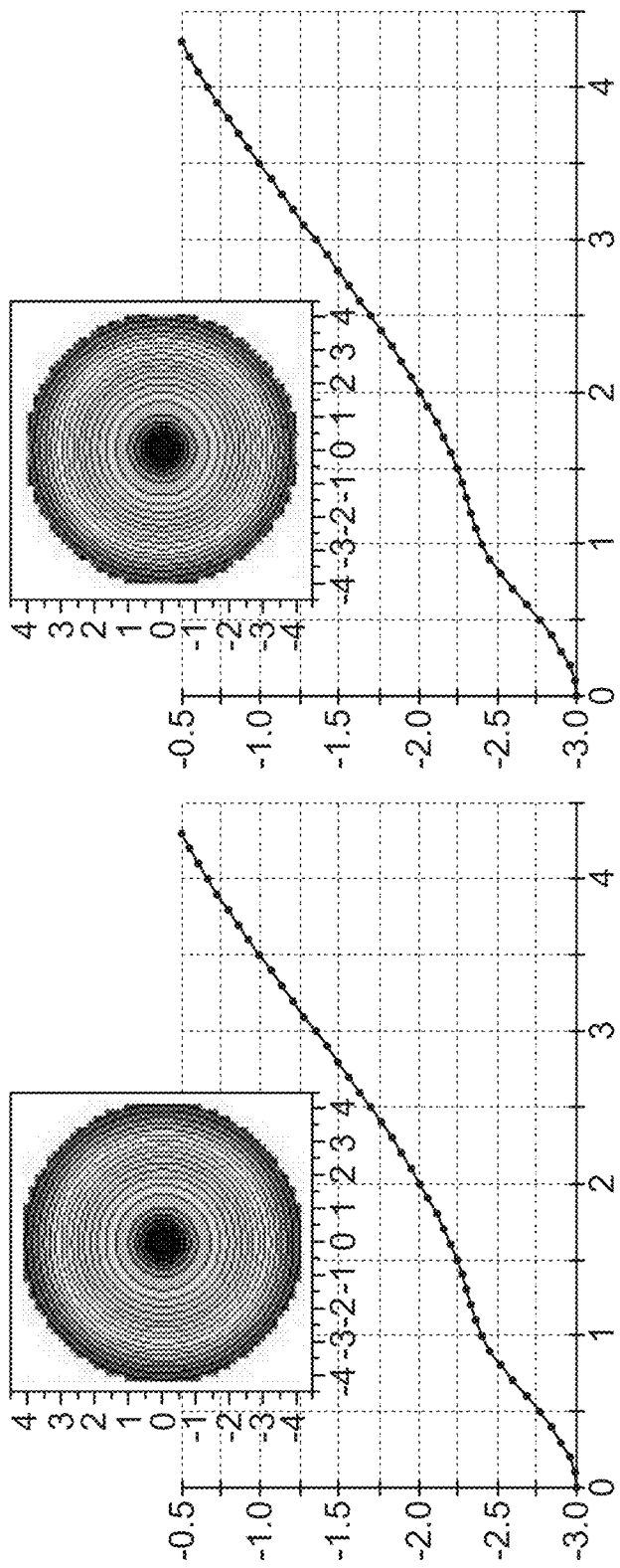
Figure 12C:
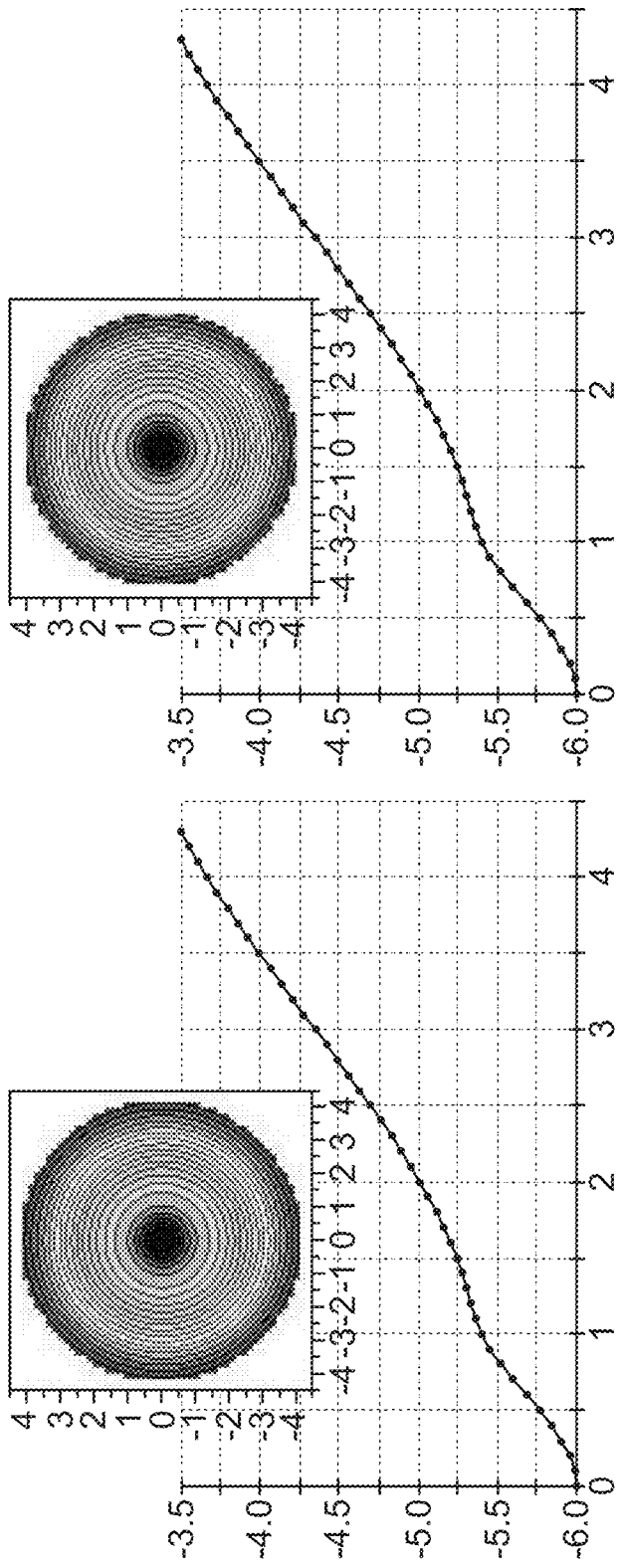

FIG. 12 shows the detailed power profile plots of specific spherical lens designs generated by this method with apical powers of −1.00 DS, −3.00 DS, and −6.00 DS. The profiles shown are the powers on axis and going out into the periphery of the optical zone of the lens.

Figure 13A:
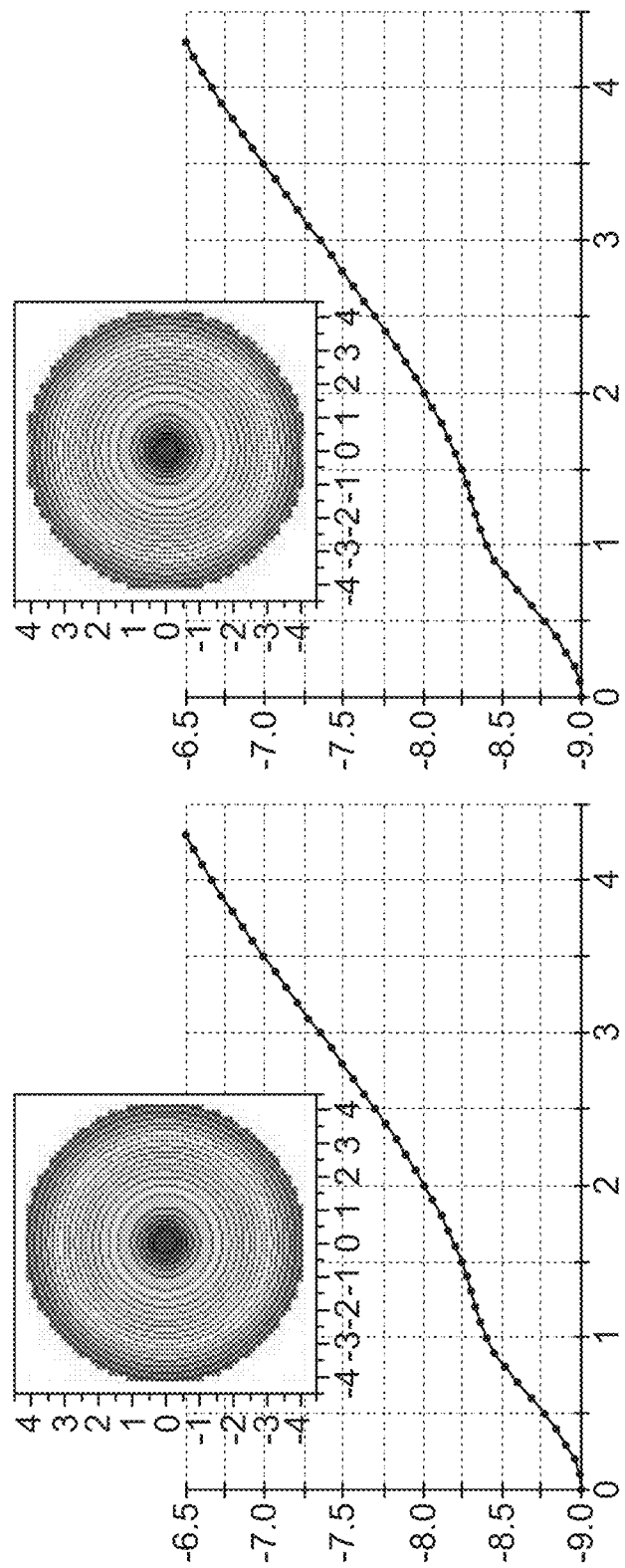
FIGS. 13A-13C show power profiles of lenses designed according to an aspect of the inventive method.
Figure 13B:
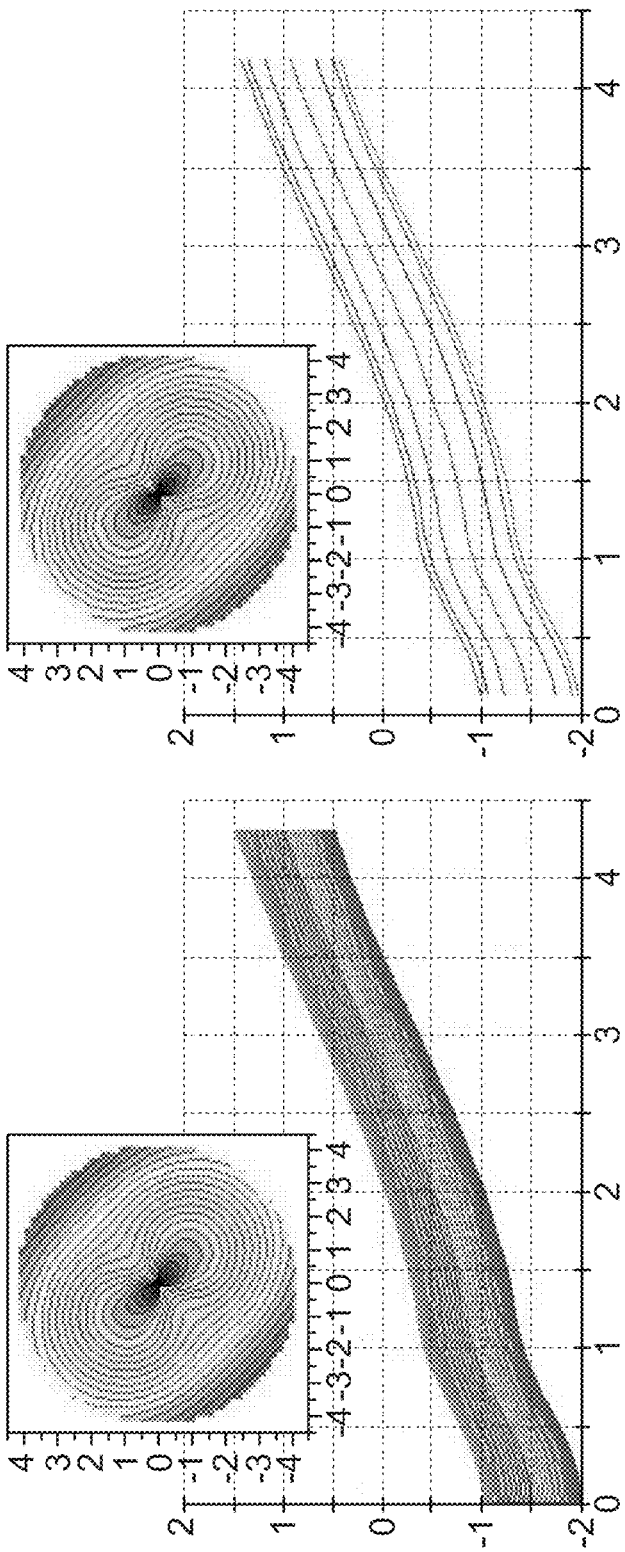
Figure 13C:
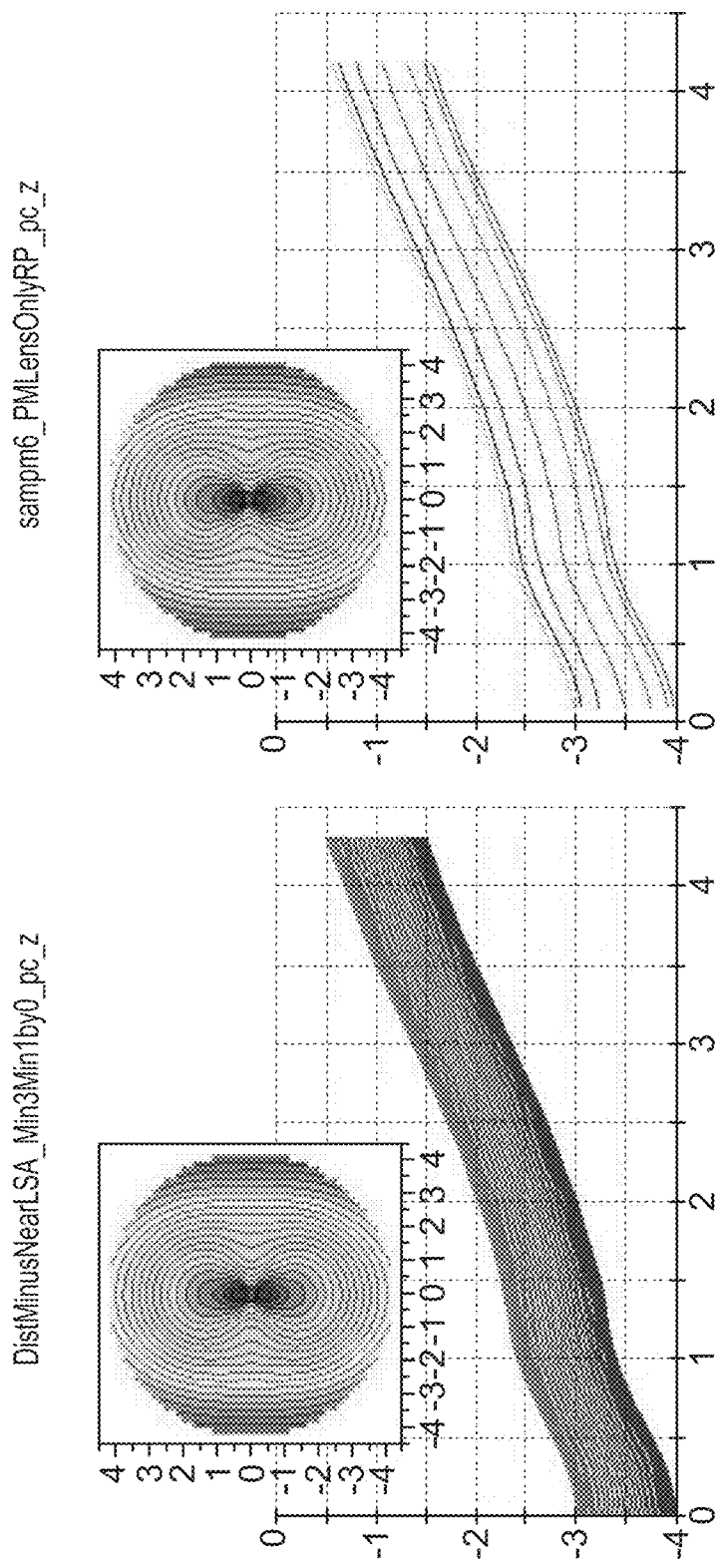

FIG. 13 shows the detailed power profile plots of a specific spherical lens design generated by this method with apical powers of −9.00 DS, and toric designs of −1.00DS−1.00 DC×45, and −3.00 DS−1.00 DC×0. The profiles shown are the powers on axis and going out into the periphery of the optical zone of the lens.

Figure 14A:
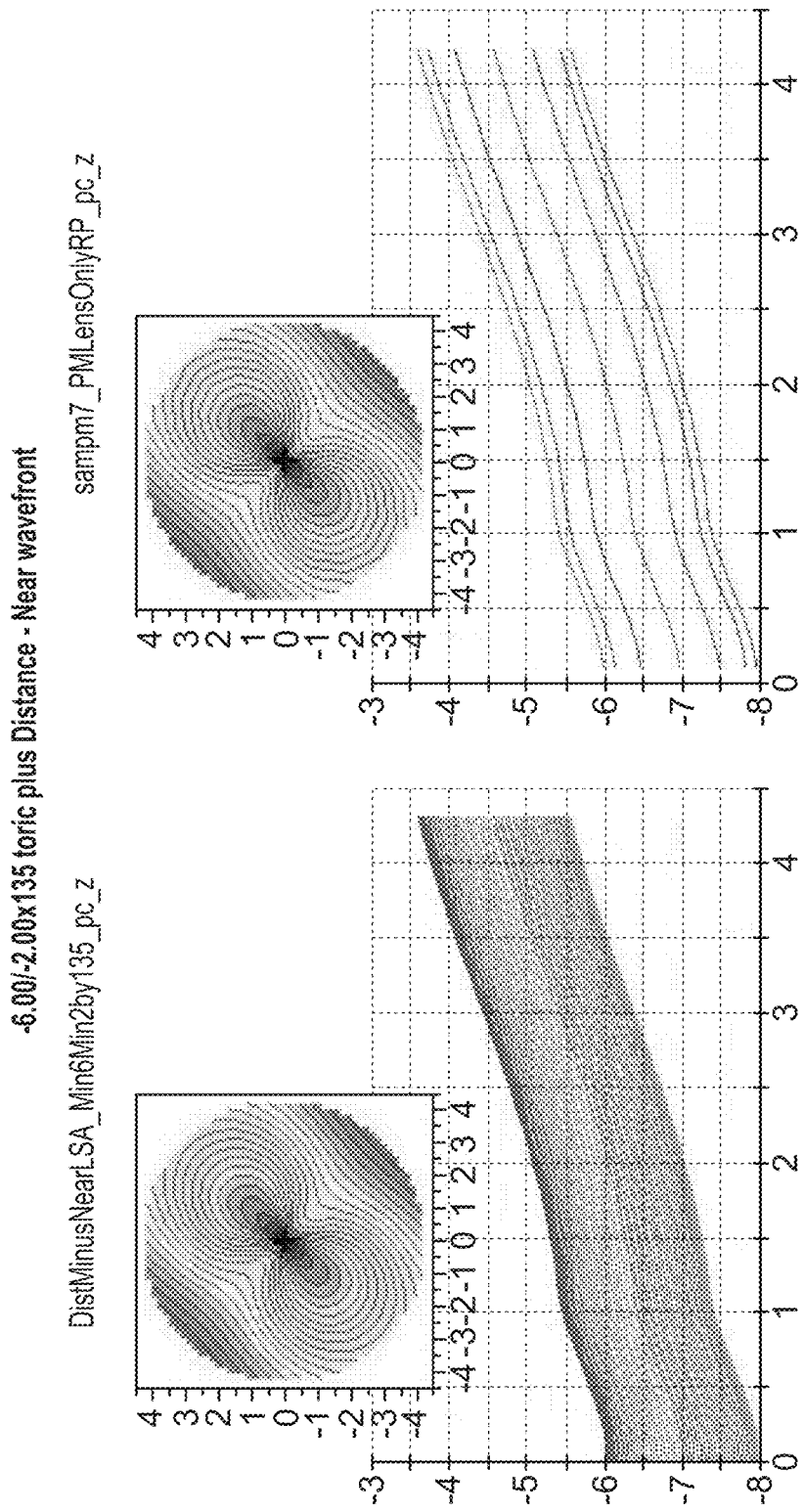
FIGS. 14A-14B show power profiles of lenses designed according to an aspect of the inventive method.
Figure 14B:
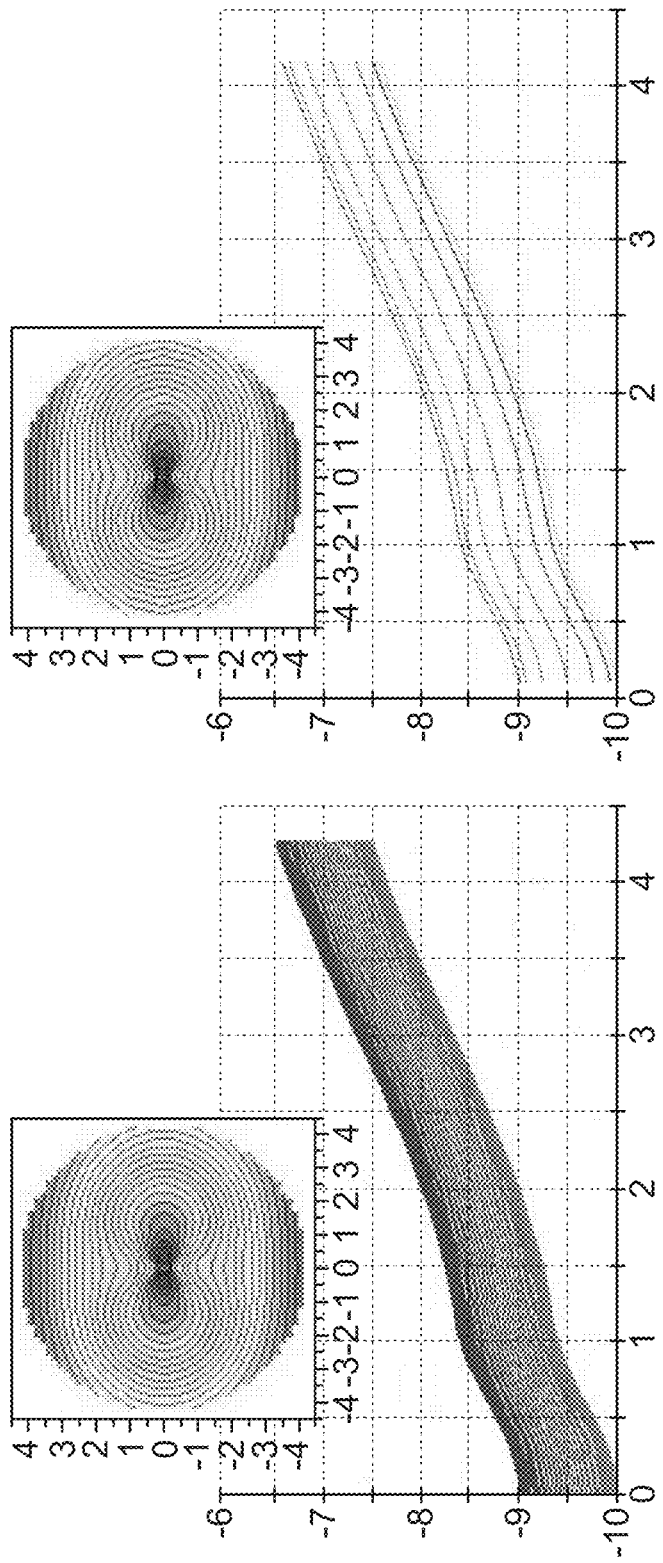

FIG. 14 shows the detailed power profile plots of specific astigmatic or toric lens designs generated by this method with apical powers of −6.00DS−2.00 DC×135, and −9.00 DS−1.00 DC×90. The profiles shown are the powers on axis and going out into the periphery of the optical zone of the lens.

The methods of the invention can be embodied as computer readable code on a computer readable medium. The computer readable medium is any data storage device that can store data, which thereafter can be read by a computer system. Examples of computer readable medium include read-only memory, random-access memory, CD-ROMs, DVDs, magnetic tape, optical data storage devices. The computer readable medium can also be distributed over network coupled computer systems so that the computer readable code is stored and executed in a distributed fashion.

The invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

Devices according to the invention may also be one or more processing systems including, but not limited to, a central processing unit (CPU), memory, storage devices, communication links and devices, servers, I/O devices, or any subcomponents of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

One skilled in the art of computer science will readily be able to combine the software created as described with appropriate general purpose or special purpose computer hardware to create a computer system or computer sub-system embodying the method of the invention.

The methods embodied in, for example, the computer instructions on computer readable media are used to produce the designs described above. The designs created according to one of the methods described above are used to produce lenses. Preferably, the lenses are contact lenses. Illustrative materials for formation of soft contact lenses include, without limitation, silicone elastomers, silicone-containing macromers including, without limitation, those disclosed in U.S. Pat. Nos. 5,371,147, 5,314,960, and 5,057,578 incorporated in their entireties by reference, hydrogels, silicone-containing hydrogels, and the like and combinations thereof. More preferably, the surface is a siloxane, or contains a siloxane functionality including, without limitation, polydimethyl siloxane macromers, methacryloxypropyl siloxanes, and mixtures thereof, silicone hydrogel or a hydrogel. Illustrative materials include, without limitation, acquafilcon, etafilcon, genfilcon, lenefilcon, senefilcon, balafilcon, lotrafilcon, or galyfilcon.

Curing of the lens material may be carried out by any convenient method. For example, the material may be deposited within a mold and cured by thermal, irradiation, chemical, electromagnetic radiation curing and the like and combinations thereof. Preferably, molding is carried out using ultraviolet light or using the full spectrum of visible light. More specifically, the precise conditions suitable for curing the lens material will depend on the material selected and the lens to be formed. Suitable processes are disclosed in U.S. Pat. Nos. 4,495,313, 4,680,336, 4,889,664, 5,039,459, and 5,540,410 incorporated herein in their entireties by reference.

The contact lenses of the invention may be formed by any convenient method. One such method uses a lathe to produce mold inserts. The mold inserts in turn are used to form molds. Subsequently, a suitable lens material is placed between the molds followed by compression and curing of the resin to form the lenses of the invention. One ordinarily skilled in the art will recognize that any other number of known methods may be used to produce the lenses of the invention.

We claim:

1. A method of designing contact lenses, the method comprising the steps of:
   a) acquiring ocular wavefront data from one or more individuals;
   b) converting the acquired ocular wavefront data to a refractive power map;
   c) generating a lens power profile that includes correction factors for near and far vision based on the acquired ocular wavefront data and measured pupil size the lens design power profile is calculated by averaging all meridians to a rotationally symmetric form,
   d) fabricating contact lenses from the lens power profile.

2. The method of claim 1 wherein the wavefront data is acquired from a total population.

3. The method of claim 1 wherein the wavefront data is acquired from a sub-population.

4. The method of claim 1 wherein the wavefront data is acquired from an individual.

5. The method of claim 1 wherein the wavefront data is an average of multiple wavefront files.

* * * * *